(12) United States Patent
Shionoya et al.

(10) Patent No.: US 6,350,863 B1
(45) Date of Patent: Feb. 26, 2002

(54) 3, 4-DI(ACYLAMINO)PHENYL RIBOFURANOSIDES, 2'-DEOXYRIBOFURANOSIDES, AND METHODS OF MAKING

(75) Inventors: Mitsuhiko Shionoya; Kentaro Tanaka, both of Okazaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/448,596

(22) Filed: Nov. 24, 1999

Related U.S. Application Data

(62) Division of application No. 09/037,609, filed on Mar. 10, 1998, now Pat. No. 6,011,143.

(30) Foreign Application Priority Data

Sep. 12, 1997 (JP) .............................................. 9-248787

(51) Int. Cl.$^7$ ........................ C07H 15/00; C07H 17/00
(52) U.S. Cl. ..................... 536/4.1; 536/27.11; 536/29.2
(58) Field of Search ................................. 536/4.1, 29.2, 536/27.11

(56) References Cited

U.S. PATENT DOCUMENTS

| | | | | |
|---|---|---|---|---|
| 4,818,761 A | * | 4/1989 | Sato et al. | .................. 514/341 |
| 5,739,022 A | * | 4/1998 | Burstyn et al. | ............. 435/184 |
| 6,011,143 A | * | 1/2000 | Shionoya et al. | .......... 536/23.1 |

FOREIGN PATENT DOCUMENTS

| | | |
|---|---|---|
| JP | 63-022091 | 1/1988 |
| JP | 63-179870 | 7/1988 |

OTHER PUBLICATIONS

Gao et al., "Crystallographic Studies of Metal–Ion–DNA Interactions: Different Binding Modes of Cobalt(II), Copper (II) and Barium (II) to $N^7$ of Guanines in Z–DNA and a Drug–DNA Complex," *Nucleic Acids Research*, 21(17), 4093–4101 (Aug. 25, 1993).*

Kalvoda et al., "Acid–Catalyzed C–Ribofuranosylation of Benzene Derivatives: Some Novel Conversions of C–Ribofuranosl Derivatives," *Coll. Czech. Chem. Comm.,* 38(6), 1679–1692 (1973).*

Scheller et al., "A Proton Nuclear Magnetic Resonance Study of Purine Pyrimidine Nucleoside 5'–Diphosphates. Extent of Macrochelate Formation in Monomeric Metal Ion Complexes and Promotion of Self–Stacking by Metal Ions," *J. American Chemical Society,* 105(18), 5891–5900 (Sep. 7, 1983).*

Shirotake, "Complexes Between Nucleic Acid Bases and Bivalent Metal Ions. III. Synthesis and Spectral Analyses of Cytosine–Calcium Chloride Complexes," *Chemical & Pharmaceutical Bulletin,* 28(3), 956–963 (Mar., 1980).*

Kikuchi et al., "Synthesis and Self–Cleavage Reaction of a Chimeric Molecule Between RNase P–RNA and Its Model Substrate," *Journal of Biochemistry,* 117(1), 197–200 (Jan. 1995).*

Battistuzzi et al., "Silver(I) Complexes of 4,6–Dimethylpyrimidine–2(1H)–thione," *Canadian Journal of Chemistry,* 59(3), 591–596 (Feb. 1, 1981).*

Summers, "Zinc Finger Motif for Single–Stranded Nucleic Acids? Investigation by Nuclear Magnetic Resonance," *Journal of Cellular Biochemistry,* 45(1), 41–48 (Jan. 1991).*

\* cited by examiner

*Primary Examiner*—Ralph Gitomer
*Assistant Examiner*—Lawrence E. Crane
(74) *Attorney, Agent, or Firm*—Fitzpatrick, Cella, Harper & Scinto

(57) ABSTRACT

Provided is an artificial nucleic acid which has a double-stranded structure made of two oligonucleotides, where the oligonucleotide has in a sugar-phosphate backbone structure thereof a sugar moiety having a group having a metal-coordinating site, and the two oligonucleotides are bound together through a metal complex structure formed by coordination of the metal-coordinating site to a metal ion. Also provided is a nucleotide useful for synthesizing the artificial nucleic acid.

4 Claims, 3 Drawing Sheets

3,4-DI(ACYLAMINO)PHENYL RIBOFURANOSIDES, 2'-DEOXYRIBOFURANOSIDES, AND METHODS OF MAKING

This application is a divisional of U. S. application Ser. No. 09/037,609 filed on Mar. 10, 1998, now U.S. Pat. No. 6,011,143, which claims priority from Japanese Patent Application No.9-248 787, filed Sep. 12, 1997.

BACKGROUND OF THE INVENTION

1. Field of the Invention

The present invention relates to an artificial nucleic acid which is expected to be used as a novel electric, optical, or magnetic functionalized material such as a molecular electric wire, and a production method thereof. The present invention also relates to a ribofuranose compound and a deoxyribofuranose compound which are effective for the efficient synthesis of the artificial nucleic acid above and a production method thereof.

2. Related Background Art

Biomolecules have ingeniously controlled higher-order structures and unique functions come of the structure. It is expected that artificial biomaterials having completely new functions can be produced by mimicking these higher-ordered structures. In particular, nucleic acids (such as DNA and RNA) are a promising material for a novel material having an electric, optical, or magnetic function, for example, a molecular electric wire, other than the information-storing function.

SUMMARY OF THE INVENTION

The present invention has been made in view of the above-mentioned active utilization of nucleic acids. An object of the present invention is to provide a novel structured material having a double-stranded structure similar to a natural nucleic acid to which various functions can be introduced (hereinafter referred to as "an artificial nucleic acid"). Another object of the present invention is to provide a method for synthesizing the artificial nucleic acid. Yet another object of the present invention is to provide a ribofuranose compound and a deoxyribofuranose compound, which are useful intermediates for efficient synthesis of the artificial nucleic acid.

To accomplish the above-mentioned objects, one aspect of the present invention provides an artificial nucleic acid having a double-stranded structure constituted of two oligonucleotides each of which has a group having a metal-coordinating site where the group is attached to a sugar moiety of a sugar-phosphate backbone of the oligonucleotide, wherein the two oligonucleotides are bound to form the double-stranded structure through a metal complex structure formed by coordination of the metal-coordinating site to a metal ion.

An example of the artificial nucleic acid is an artificial nucleic acid having a structure represented by the following formula (10):

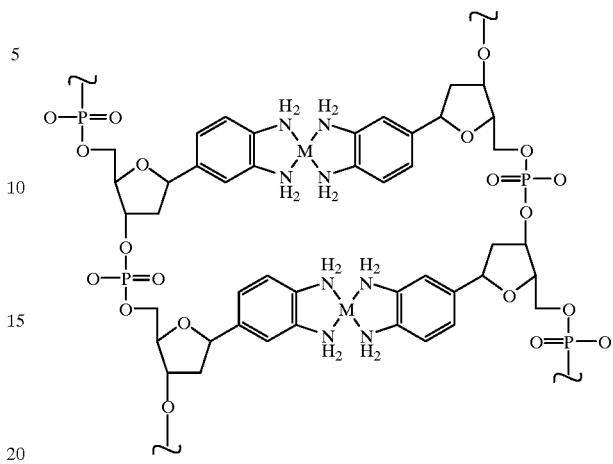

(10)

where M represents a metal selected from the group consisting of zinc (Zn), nickel (Ni), and platinum (Pt).

According to another aspect of the present invention, there is provided a method for synthesizing an artificial nucleic acid having a double-stranded structure constituted of two oligonucleotides each of which has a group having a metal-coordinating site where the group is attached to a sugar moiety of a sugar-phosphate backbone of the oligonucleotide, and the two oligonucleotides are bound to form the double-stranded structure through a metal complex structure formed by coordination of a metal coordinating site to a metal ion, wherein the method comprises the steps of:

synthesizing an oligonucleotide from nucleotides containing a nucleotide having a group having a metal-coordinating site attached to a sugar moiety of the nucleotides employing a phosphoramidite method; and binding two of the oligonucleotide and forming the double-stranded structure by coordinating the metal coordinating site to the metal ion, and forming a metal complex structure between the oligonucleotides.

According to one aspect of the present invention, there is provided a ribofuranose compound having a structure represented by the following constitutional formula (11):

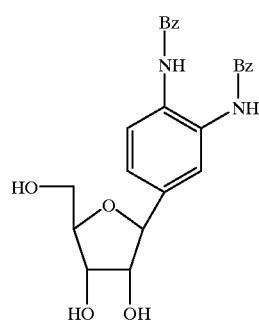

(11)

where Bz represents benzoyl.

According to another aspect of the present invention, there is provided a synthetic method for a ribofuranose compound having a structure represented by the following constitutional formula (11):

(11)

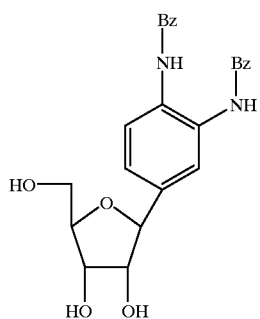

where Bz represents benzoyl; which comprises the steps of:
(i) by reacting 1-bromo-3,4-diaminobenzene and 1,2-bis(chlorodimethylsilyl)ethane in an anhydrous solvent followed by lithiation to form a compound of following formula (15);

(15)

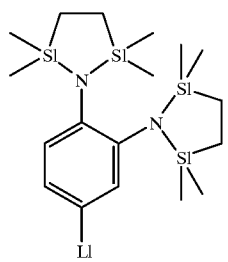

(ii) reacting the compound of formula (15) and 2,3,5-tri-o-benzyl ribonolactone followed by converting each 2,5-disilapyrrolidinyl group on the benzene ring to an amino group; and
(iii) protecting the amino group with a benzoyl group followed by converting the benzyloxy groups at 2', 3', 5' positions of the ribofuranose ring to a hydroxyl group.

According to another aspect of the present invention, there is provided a deoxyribofuranose compound having a structure represented by the following constitutional formula (12):

(12)

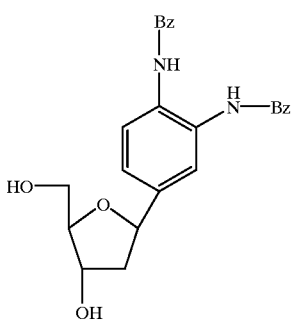

where Bz represents benzoyl.

According to another aspect of the present invention, there is provided a synthetic method for a deoxyribofuranose compound having a structure represented by the following constitutional formula (12):

(12)

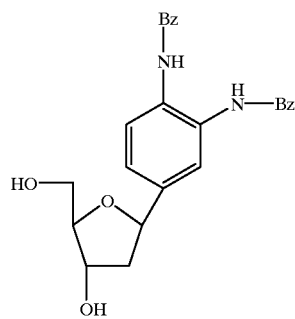

where Bz represents benzoyl; which comprises the steps of:
(i) by reacting 1-bromo-3,4-diaminobenzene and 1,2-bis(chlorodimethylsilyl)ethane in an anhydrous solvent followed by lithiation to form a compound of following formula (15);

(15)

(ii) reacting the compound of formula (15) and 2,3,5-tri-o-benzyl ribonolactone followed by converting each 2,5-disilapyrrolidinyl group on the benzene ring to an amino group;
(iii) protecting the amino group with a benzoyl group followed by converting benzyloxy groups at 2', 3', 5' positions of the ribofuranose ring to hydroxyl group; and
(iv) protecting the hydroxyl groups at the 3' and 5' of the ribofuranose ring, removing the hydroxyl group at 2' of the ribofuranose ring, and deprotecting the hydroxyl groups at positions 3' and 5' of the ribofuranose ring.

According to the present invention, there is provided an artificial nucleic acid having a double-stranded structure as natural nucleic acids have, to which various functions can be introduced.

DETAILED DESCRIPTION OF THE PREFERRED EMBODIMENTS

Figure 1:
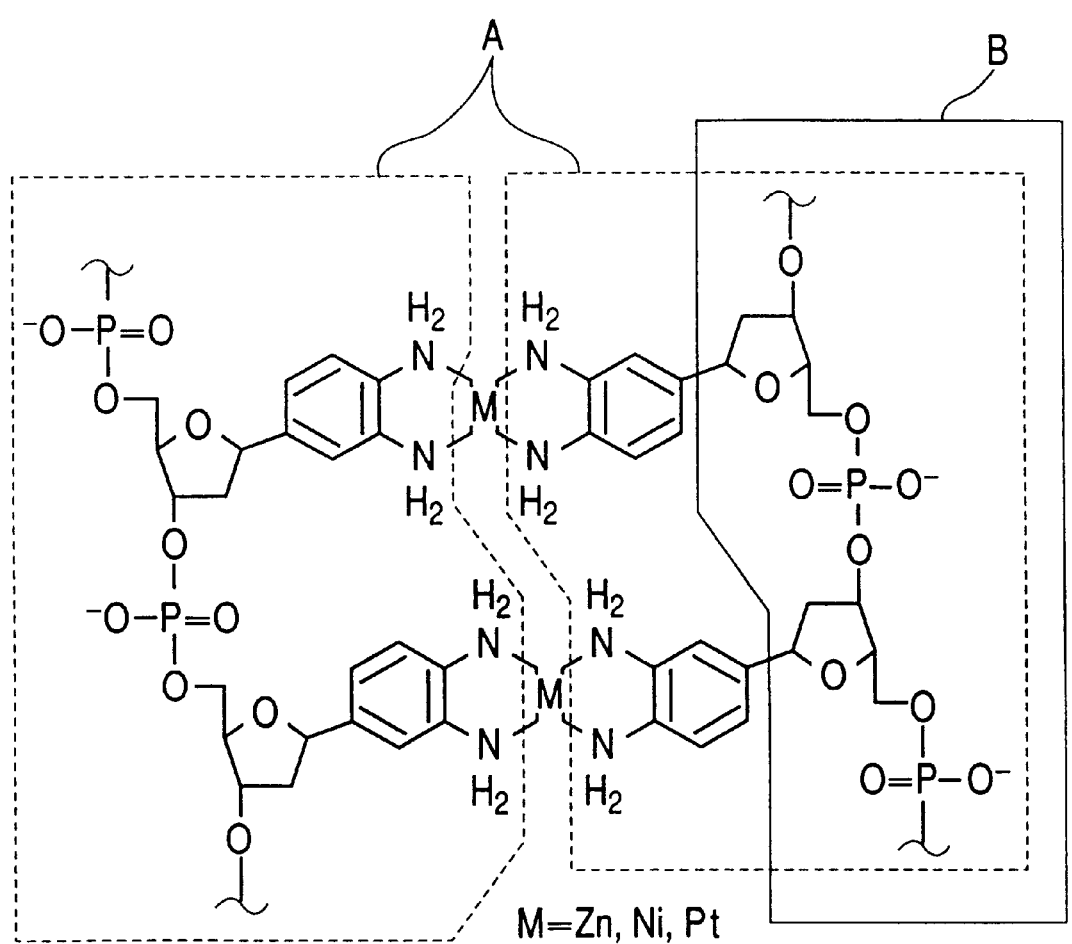
FIG. 1 is a diagram showing the molecular structure of one example of an artificial DNA according to the present invention, wherein A corresponds to the oligonucleotide portion, and B corresponds to the sugar-phosphate backbone portion.

An artificial nucleic acid of the present invention has a double-stranded structure made of two oligonucleotides, where each oligonucleotide has in a sugar-phosphate backbone structure thereof at least one sugar moiety having a group having a metal-coordinating site, and the two oligonucleotides are bound together through a metal complex structure formed by coordination of the metal-coordinating site to a metal ion. FIG. 1 shows an illustrative structure of an artificial nucleic acid having double-stranded structure. The structure shown in FIG. 1 is a schematic molecular model of an artificial deoxyribonucleic acid (artificial DNA). The artificial DNA comprises two oligonucleotides (A) and metal ions (M), and at least one metal complex structure is formed between two oligonucleotide due to the coordinate bond formed between a metal ion and metal-coordinating sites provided on sugar moieties of the oligonucleotides.

In this example, a phenyl group having two amino groups as a metal-coordinating site is attached to a deoxyribofuranose ring at position 1', and this sugar moiety constitutes the sugar-phosphate backbone of the oligonucleotide. By the coordination of the amino groups to a metal ion (M), the two oligonucleotides are held together so as to form a double-stranded structure similar to a natural DNA.

Natural DNA has a double helix structure held by hydrogen bonding between complementary base pairs. On the other hand, the artificial DNA has a double-stranded structure held by a metal complex structure formed between a metal ion and a metal-coordinating site of a group attached to a sugar moiety into the oligonucleotide, instead of hydrogen bonding. Because of this structure, the DNA structure originally bearing genetic information can be applied for a functional material. According to this structure of the artificial nucleic acid, the metal-coordinating site can be introduced to any sugar moiety of the oligonucleotide. For example, it is possible to synthesize an oligonucleotide having metal-coordinating sites in line by polymerizing nucleotides each substituted with a group having a metal-coordinating site. One can expect an excellent function as a so-called molecular wire from an artificial nucleic acid obtained by coordinating the above polynucleotides to metal ions, since electrons can move along metal ions continuously aligned in the double strands.

In the artificial DNA of FIG. 1, the central metal ion (M) to form a complex structure with ligands is exemplified by zinc, nickel, and platinum etc. In particular, the platinum ion is preferable due to its strong bonding with ligands to provide a stable complex.

In FIG. 1, o-phenylene diamine (3,4-diaminophenyl) is used as a group having a metal-coordinating site, but not limited thereto. In the present invention, any ligand can be used so long as the size after the complex formation with the metal ion corresponds to that of a base pair in natural nucleic acid. For example, there are phenyl, maleimide, and pyrimidine groups substituted at two positions with metal-coordinating groups. Example of metal-coordinating groups include hydroxyl, amino, and thiol. Examples of phenyl groups having a metal-coordinating site include a phenyl group of which 3 and 4 carbons are substituted with hydroxyl, amino or thiol independently, such as the following examples (1) to (6).

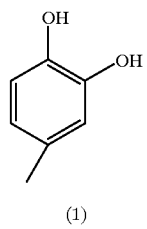

(1)

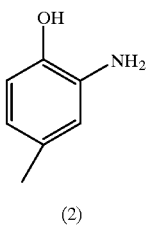

(2)

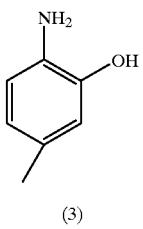

(3)

-continued

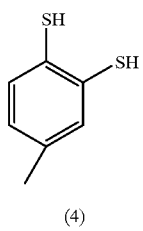

(4)

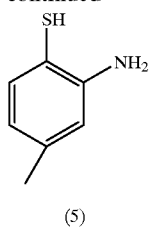

(5)

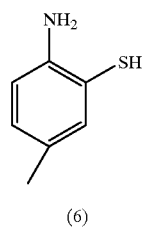

(6)

Examples of maleimide groups or pyrimidine groups having a metal-coordinating site include the following structures (7) to (9).

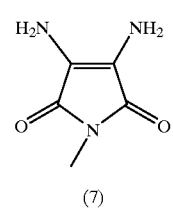

(7)

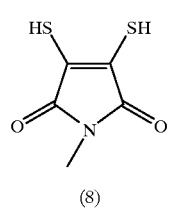

(8)

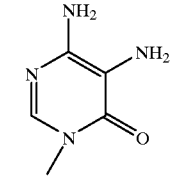

(9)

The number of riboses substituted with a group having a metal-coordinating site in an oligonucleotide constituting the double-stranded structure of an artificial DNA can be selected in a range of one or more, according to the application of the artificial DNA.

Although FIG. 1 shows an example of an artificial DNA, the kind of nucleic acid can be selected according to the purpose. For example, artificial RNAs are also useful.

The artificial DNA shown in FIG. 1 can be synthesized by the following method.

A single-stranded oligonucleotide for a double-stranded oligonucleotide can be obtained by the following method. An artificial nucleoside, e.g. a deoxyribofuranose compound represented by the following formula (12), is prepared by replacing the base portion of a natural nucleoside with 3,4-diaminophenyl. The detailed synthetic method of the nucleoside will be described later.

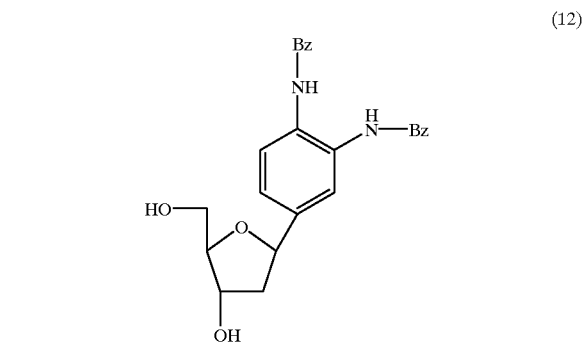

(12)

Then the hydroxyl group at 5' position of the deoxyribofuranose is dimethoxytritylated and the hydroxy at 3' is amidited to obtain a phosphate derivative of the nucleoside (nucleotide). In order to obtain an artificial oligonucleotide for forming an artificial DNA shown in FIG. 1, these nucleotides are subjected to block synthesis by the phosphoramidite method, a popular method for nucleic acid synthesis, using a DNA synthesizer. Finally, protective benzoyl and trityl groups are removed from the product. In the field of DNA synthesis, a method for synthesizing nucleic acid of any base order has been established. Using a commercially available DNA synthesizer, an oligonucleotide, for example 50-mer or more of nucleotides, can be easily obtained, where the hydroxyl group at the 5' of a nucleoside (a deoxyribose to which a base (adenine, guanine, cytosine, or thymine) is bonded by N-glycoside bonding at 1') is dimethoxytritylated and the 3' hydroxy group is amidited to obtain a phosphate derivative of the nucleoside (i.e. nucleotide), and these nucleotides are placed in an automatic synthesizer designating a certain base sequence. Using a DNA synthesizer for the block synthesis by the phosphoramidite method, an artificial oligonucleotide having metal-coordinating sites can be obtained from nucleosides represented by the above-mentioned formula (12), and various natural nucleosides. When such a system is used, it is possible to obtain an artificial oligonucleotide where ligands are located at optional positions among various nucleotides. Then, two oligonucleotides are formed into a double-stranded artificial DNA by coordinating each metal-coordinating site to a metal ion (M).

A method for synthesizing a deoxyribofuranose compound having a structure represented by the above-mentioned formula (12) will be explained. The compound can be synthesized according to the scheme shown in FIG. 2. First, 4-bromo-phenylene diamine (compound 13) is synthesized. The synthesis can be conducted by a method disclosed in Japanese Laid-Open Patent Application Nos. 63-22091 and 63-179870. Specifically, o-phenylene diamine is added to acetic acid, and further mixed with acetic anhydride under cooling, and the resultant reaction mixture is heated. After cooling, a bromine solution in acetic acid is slowly added to the reaction mixture. Then, an acidic sodium sulfite solution dissolved in ice water is added into the reaction mixture. The resultant white precipitate is collected to obtain compound 13, 4-bromo-o-phenylene diamine. By reacting compound 13 and 1,2-bis(chlorodimethylsilyl) ethane, compound 14 of which two amino groups attached to the benzene ring are protected, can be obtained. By lithiating compound 14 by reacting with butyl lithium (n-BuLi), compound 15 can be obtained. Then, 2,3,5-tri-o-benzyl ribonolactone (compound 16) dissolved in THF (20 ml) is reacted with compound 15. The protecting groups of the amino groups on the benzene ring are removed by using trifluoroborane and triethylsilane to obtain compound 17. Compound 18 can be obtained by treating compound 17 with benzoyl chloride. Treatment of compound 18 with boron tribromide in dichloroethane to convert all benzyloxy groups at 2', 3' and 5' positions of compound 18 to hydroxyl groups gives ribofuranose compound 11. Then compound 11 is reacted with 1,3-dichloro-1,1,3,3-tetraisopropyldisiloxane so as to obtain compound 19 where 3' and 5' hydroxyl groups of the ribofuranose compound 11 are protected. The hydroxyl group at the 2' position of compound 19 is reacted with p-trichlorothinoformate so as to obtain compound 20. Compound 20 is reacted with tributyltin hydride in the presence of a catalytic amount of azoisobutylonitrile (AIBN) to obtain compound 21. By reacting compound 21 with tetrabutyl ammonium fluoride in THF at room temperature to remove the protection group, a deoxyribonucleoside having a deoxyribofuranose ring represented by the above-mentioned formula 12, which does not have a hydroxyl group at the 2' position, can be obtained.

In each reaction process in the above-mentioned synthetic method, ordinarily used reaction conditions can be used.

Although the artificial nucleic acid shown in FIG. 1 has a structure based on DNA, that is, the sugar-phosphate backbone has a structure similar to that of DNA, those having the basic structure of RNA can also be used. Specifically, compound 11 in the scheme of FIG. 2 can be used as the nucleoside. After the hydroxyl groups at the 5' position and the 2' position are protected with a dimethoxytrityl group and a tert-butyl dimethylsilyl group using tert-butyl-dimethyl-silyl chloride respectively, the hydroxyl group at the 3' position is amidited to obtain a phosphate derivative of the nucleoside (nucleotide). Using an automatic DNA synthesizer, the nucleotides are subjected to the block synthesis by the phosphoramidite method, an ordinary method for synthesizing nucleic acid, so as to obtain an oligonucleotide. Next, benzoyl and trityl groups are removed and then the tert-butyl dimethylsilyl group at the 2' position of the ribofuranose is removed using tetrabutyl ammonium fluoride to obtain an artificial oligonucleotide having an RNA backbone instead of DNA backbone of FIG. 1. By coordinating the artificial oligonucleotide to metal ions, an artificial double-stranded RNA can be obtained.

Figure 2:
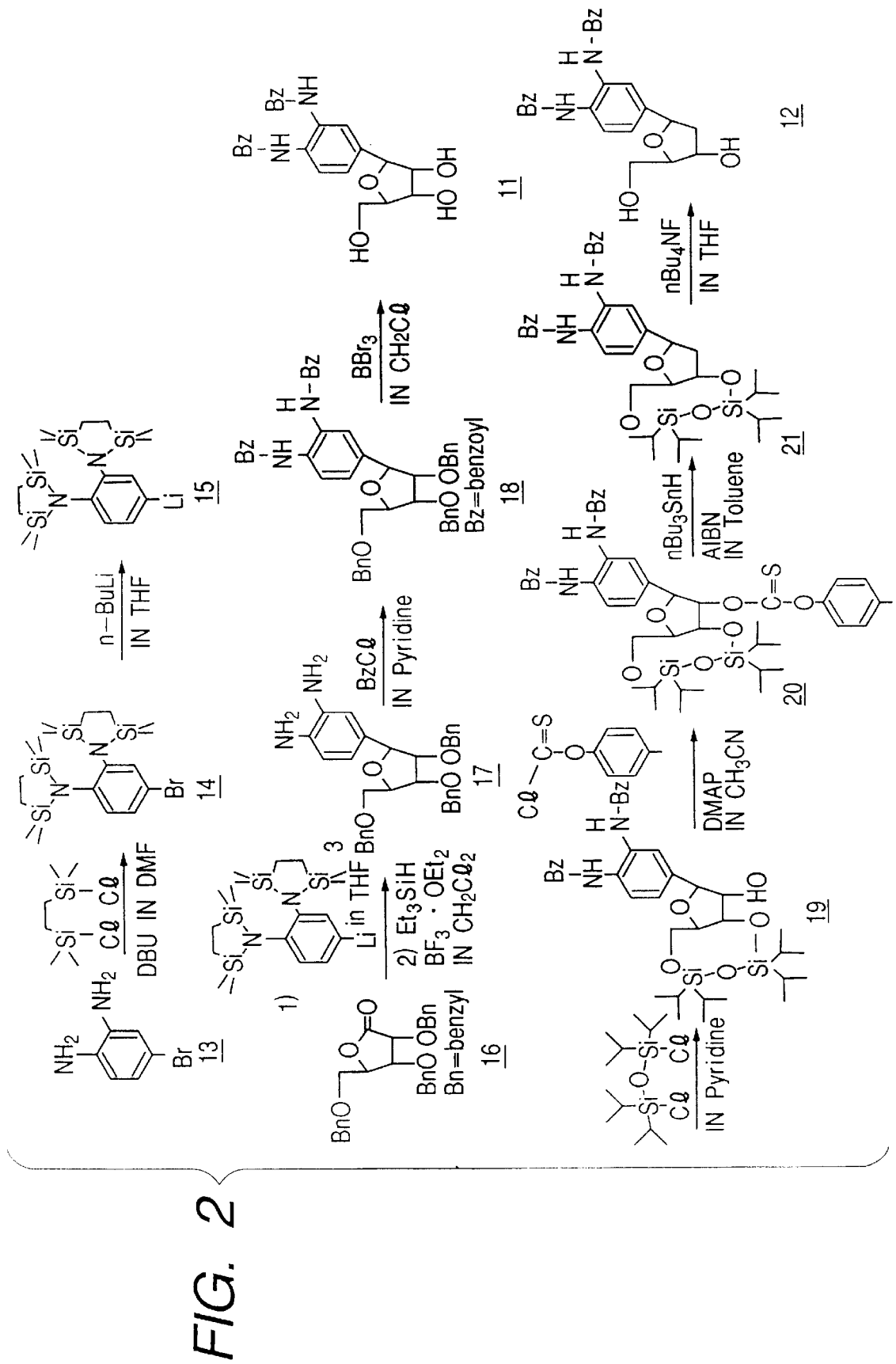
FIG. 2 is a synthesis protocol of a ribofuranose compound or a deoxyribofuranose compound usable for the synthesis of the artificial nucleic acid of the present invention.
Figure 3:
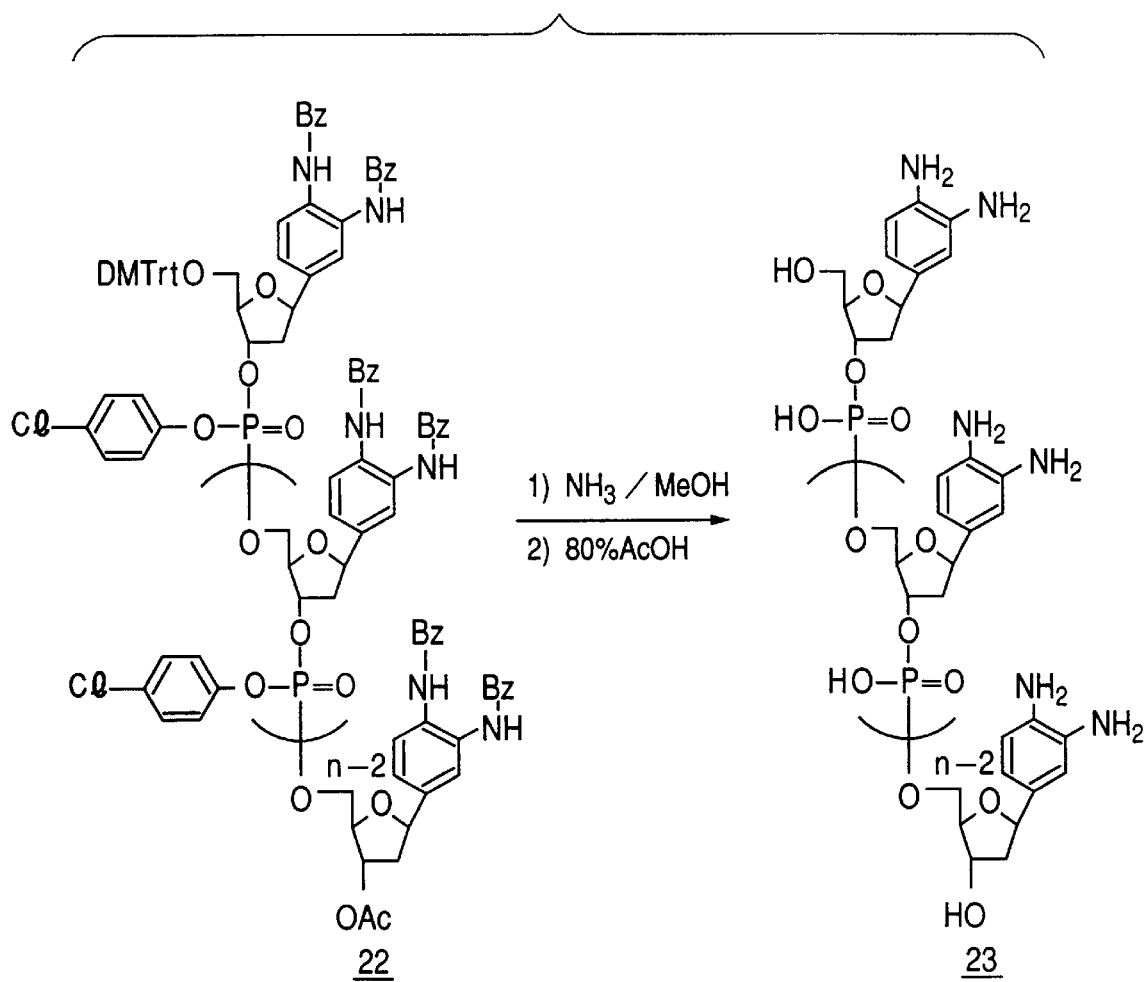
FIG. 3 illustrates an example of a step removing the trityl group and protecting groups from an artificial nucleic acid according to the present invention.

Hereinafter the present invention will be explained in further detail by examples with reference to FIGS. 2 and 3.

EXAMPLE 1

Synthesis of an Artificial Nucleoside having o-phenylene Diamine as a Ligand (Compounds 11 and 12)

(1) Synthesis of 4-bromo-o-phenylene Diamine (Compound 13)

In 64 ml of acetic acid, 8.0 g of o-phenylene diamine was dissolved, to which 15.3 ml of acetic anhydride was added drop-wise under cooling. Then the mixture was heated for 30 minutes in an oil bath at 65° C. After cooling to room temperature, a solution of bromine (4.6 ml bromine in 16 ml acetic acid) was quickly added, followed by heating for 40 minutes in an oil bath at 50° C. About 10 minutes after adding bromine, crystals started to precipitate. The reaction mixture was cooled to room temperature, and poured into 300 ml ice water containing 4.0 g sodium hydrogen sulfite. The resulting white precipitates were collected by filtration, washed with water and dried under reduced pressure (14.0 g; yield 70%). Into a 150 ml solution of water: methanol (2:1) containing 33.6 g potassium hydroxide, the white solid was dissolved and heated with stirring for 12 hours in an oil bath at 75–80° C. After cooling the reaction mixture, and adding 400 ml water thereto, the mixture was extracted with 100 ml ether five times. The ether phase was washed with 200 ml of saturated salt water two times, and dried with anhydrous sodium sulfate. The solvent was evaporated under reduced pressure. The residue was purified by silica gel column chromatography (hexane ethyl acetate=3:1 to 1:1) so as to obtain compound 13 as colorless crystals (5.5 g, total yield 40%).

(2) Synthesis of Compound 14

In 20 ml of dry dimethyl formamide (DMF), 4.36 g of 4-bromo-o-phenylene diamine (compound 13) was dissolved, to which 14.9 ml 1,8-diazabicyclo[5.4.0]undec-7-en and 10 ml DMF containing 10 g of 1,2-bis (chlorodimethylsilyl)ethane were added. The reaction mixture was stirred for 4 hours at 120° C., and then cooled to room temperature. The solvent was removed under reduced pressure. The residue was dissolved in 150 ml ether, washed with 100 ml of saturated salt water five times. After drying the organic phase with anhydrous sodium sulfate, the solvent was removed under reduced pressure. The obtained brown oil was passed through silica gel bed with hexane: diethyl ether=1:1 so as to obtain compound 14 as a slightly yellow oil (7.8 g; 71%).

(3) Synthesis of compound 17

In 15 ml of dry tetrahydrofuran (THF), 1.18 g of compound 14 was dissolved. At −78° C., 1.84 ml of a 1.63 M solution of n-BuLi in hexane was added thereto. After 1 hour, 0.96 g of 2,3,5-tri-o-benzyl ribonolactone (compound 16) dissolved in 5 ml of THF was added to the mixture, and the mixture was stirred for 2 hours at −78° C., then the temperature was raised to 0° C. over 3 hours. The reaction mixture, after addition of 20 ml of a saturated aqueous solution of sodium hydrogen carbonate, was extracted with 25 ml of diethyl ether four times. The organic phase was washed with 12 ml of saturated salt water, and dried with anhydrous sodium sulfate. By removing the solvent under reduced pressure, a pale brown oil was obtained. The oil was dissolved in 5 ml of methylene chloride, to which 1.83 ml of triethylsilane was added, and 1.46 ml of boron trifluoride-diethyl ether complex was added drop-wise over 15 minutes at −78° C. Then, the temperature of the reaction mixture was raised to room temperature over 5 hours. Reaction was quenched by adding 5 ml of 1 M hydrochloric acid. The mixture was further stirred for 1 hour. The reaction mixture was neutralized with a 2% sodium hydroxide aqueous solution, and extracted with 20 ml of ethyl acetate five times. The organic phase was washed with 10 ml of saturated salt water, dried with anhydrous sodium sulfate, and the solvent was removed under reduced pressure. The obtained residue was purified by silica gel chromatography (hexane: ethyl acetate=1:1) to obtain compound 17 as an yellow oil (0.19 g; 16%).

(4) Synthesis of Compound 11

In 0.8 ml of dichloromethane, 112 mg of compound 17 and 40.8 µl pyridine were dissolved. While cooling in ice bath and stirring, 61 µl of benzoyl chloride was added to the mixture followed by stirring for 4 hours at room temperature. Then 2 ml of 1 M hydrochloric acid and 2 ml of water were added to the mixture, which was extracted with 5 ml of methylene chloride five times. The organic layer was washed with a 2% sodium hydroxide aqueous solution, dried with anhydrous sodium sulfate, and the solvent was removed under reduced pressure. The crude product was purified by silica gel chromatography (hexane: ethyl acetate=3:1 to 2:1) so as to obtain compound 18 as a colorless oil (117 mg; 7%). By $^1$H-NMR, the product was found to be a 57:43 mixture of α and β. Then 117 mg of obtained compound 18 was dissolved in 2 ml of methylene chloride. While stirring at −75° C., 734 µl of 1 M boron tribromide in methylene chloride was added dropwise over 15 minutes. The reaction mixture was stirred for 4 hours at −78° C. The reaction was quenched by adding 2 ml of methanol, and the temperature of the reaction mixture was raised to room temperature over 4 hours. After removing the solvent under reduced pressure, the residue was dissolved into 10 ml methylene chloride, and washed with 10 ml of saturated salt water 4 times. The organic phase was dried with anhydrous sodium sulfate. Then the solvent was removed under reduced pressure. The residue was purified by silica gel chromatography (chloroform: methanol =9:1) so as to obtain compound 11 (β form, 4.8 mg; 7%).

Compound 11

$^1$H-NMR (270 MHz, CD OD) δ3.74 (dd, J=12.0, 4.8 Hz, 1H, C5'-H), 3.81 (dd, J=12.0, 4.3 Hz, 1H, C5"-H), 3.92 (dd, J=6.7, 5.6 Hz, 1H, c2'-H), 4.00 (ddd, J=4.2, 4.1, 4.1 Hz, 1H, C4'-H), 4.07 (dd, J=5.9, 4.1 Hz, 1H, C3'-H), 4.77 (d, J=6.6 Hz, 1H, C1'-H), 7.41–7.72 (m, 9H, Ar-H), 7.91–7.95 (m, 4H, Ar-H)

$^{13}$C-NMR (67.8 MHz, CD OD) δ64.48, 73.30, 74.33, 79.97, 85.63, 125.58, 125.88, 126.30, 126.51, 127.25, 127.71, 129.35, 129.42, 129.62, 129.67, 130.61, 131.90, 132.85, 133.29, 134.11, 136.12, 141.57, 145.25, 169.60, 169.69

(5) Synthesis of Compound 12

Into 100 µl of pyridine, 3 mg of compound 11 was added and 2 µl of 1,3-dichloro-1,1,3,3-tetraisopropyl disiloxane was added thereto and reacted for 4 hours at room temperature. After removing the solvent, 100 µl of aqueous 1 M sodium hydroxide was added. The aqueous phase was extracted with dichloromethane, and the organic phase was collected and evaporated to dryness to obtain compound 19. The obtained compound 19 was reacted with 2 µl of p-tolyl chlorothioformate in the presence of a catalytic amount of dimethylamino pyridine (DMAP) for 25 hours at room temperature. By the extraction of the reaction mixture with ethyl acetate, compound 20 was obtained. The compound 20 thus obtained was reacted with tributyltin hydride in toluene at 80° C. in the presence of a catalytic amount of azoisobutylonitrile (AIBN) to obtain compound 21. The compound 21 was reacted with tetrabutyl ammonium fluoride in THF at room temperature. With an ordinary working-up, compound 12 was obtained quantitatively.

EXAMPLE 2

Synthesis of Artificial Nucleic Acid (M=Platinum)

After dimethoxytritylating the hydroxyl group at the 5' position of deoxyribofuranose compound 12 synthesized in Example 1, the hydroxyl group at the 3' position was amidited to obtain a phosphate derivative of the deoxyribofuranose compound (nucleotide). By using the nucleotide as a reagent, two oligonucleotides each comprised of 20 nucleotides (22 of FIG. 3) were synthesized using a DNA synthesizer (produced by Applied Biosystem Corp.). Then protecting groups, i.e. trityl group at 5' end and all benzoyl groups of compound 22, were removed to obtain compound 23. By dissolving compound 23 and 0.5 equivalent of potassium platinous chloride in a tris-HCl buffer (pH 7.5), and stirring for several hours at room temperature, an artificial nucleic acid of 20 nucleotides having the structure of FIG. 1 was obtained.

The double-stranded structure formation in a solution was confirmed by high resolution nuclear magnetic resonance spectrometry (1D, COSY, NOE, imino-proton measurement) of ($^1$H, $^{13}$C $^{31}$P $^{195}$Pt), electron-spray type mass spectrometry, melting experiments by an absorbance method or circular dichroism, or pH titration.

As described above, according to the present invention, the metal-coordinating site can be introduced at any position along the base sequence in the double-stranded nucleic acid. For example, just one metal atom can be introduced in a double-stranded nucleic acid or a plurality of metal atoms can be introduced in a aligned fashion. By block synthesis of an oligonucleotide with nucleoside represented by formula (12) using an automatic DNA synthesizer, an oligonucleotide having a group having a metal-coordinating site at a desired position can be obtained. That is, by designing an artificial nucleic acid according to a function to be provided, choosing the ligand and the metal ion, and replacing a nucleotide in a natural nucleic acid with the nucleotide of the present invention, an artificial nucleic acid having a desired metal ion provided at a desired position can be easily synthesized.

Alternatively, by polymerizing nucleotides having a metal-coordinating site to synthesize an artificial oligonucleotide, an artificial nucleic acid having a structure in which metal ions are stacked one-dimensionally can be obtained. In this case, due to the aligned metal ions in the double strand structure, electrons will move along the metal ions so that an excellent function can be expected as a so-called molecular wire. Unlike the conventional molecular wires utilizing a polymer, the artificial nucleic acid of the present invention will have an advantage that the molecular weight can be controlled and long molecules can be easily synthesized. Besides, a problem of the conventional polymer molecular wires, that is, extremely poor solubility in water, may be solved by using the artificial nucleic acid of the present invention.

The nucleoside of the present invention, represented by the formula (11) or (12), is applicable to be used in oligonucleotide synthesis using an automatic DNA synthesizer. That is the amino group as the metal-coordinating site can be protected by benzoyl groups and would not react even during block synthesis using an automatic DNA synthesizer.

Furthermore, according to the method of the present invention for synthesizing a nucleoside represented by the above-mentioned formula (11) or (12), it is possible to obtain the product in high yield with much less purification steps.

Furthermore, when the artificial nucleic acid of the present invention is made into liquid crystal, an array structure of metal ion is introduced to the intrinsic lyotropic liquid crystal properties of DNA. Accordingly, application to a conductive material, a polarized material, and a magnetic material having an electronic, optical or magnetic anisotropy are expected.

What is claimed is:

1. A ribofuranose compound having a structure represented by the following formula (11):

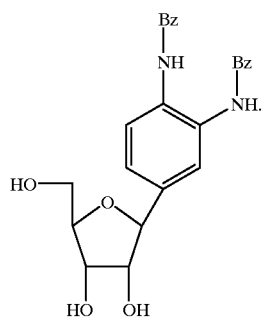

(11)

2. A method for synthesizing a ribofuranose compound having a structure represented by the following formula (11)

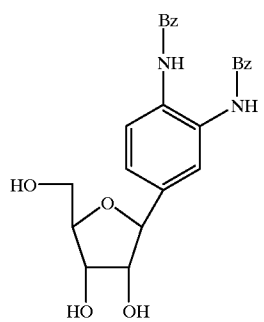

(11)

comprising the steps of:

(i) obtaining a compound represented by the following formula (15) by reacting 1-bromo-3,4-diaminobenzene and 1,2-bis(chlorodimethylsilyl)ethane in an anhydrous solvent followed by lithiation, wherein an HCl byproduct is removed prior to said lithiation;

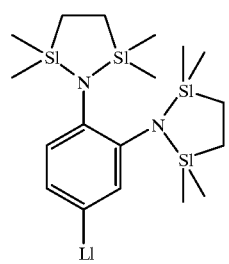

(15)

(ii) reacting the compound represented by the formula (15) and 2,3,5-tri-O-benzyl ribonolactone, and converting the 2,5-disilapyrrolidinyl groups to amino groups; and (iii) protecting the amino groups with benzoyl groups followed by deprotecting the 2', 3', and 5' positions of the ribofuranose ring.

3. A deoxyribofuranose compound having a structure represented by the following formula (12):

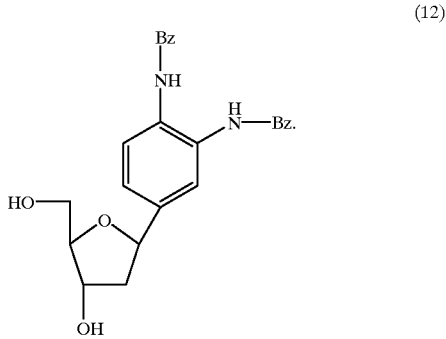

(12)

4. A method of synthesizing a deoxyribofuranose compound having a structure represented by the following formula (12)

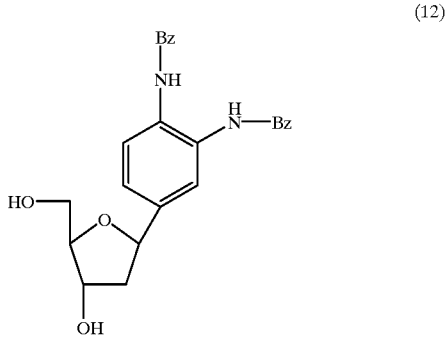

(12)

(i) obtaining a compound represented by the following formula (15) by reacting 1-bromo-3,4-diaminobenzene and 1,2-bis(chlorodimethylsilyl)ethane in an anhydrous solvent followed by lithiation, wherein an HCl byproduct is removed prior to said lithiation;

(ii) reacting the compound represented by the formula (15) and 2,3,5-tri-O-benzyl ribonolactone, and converting the 2,5-disilapyrrolidinyl groups to amino groups;

(iii) protecting the amino groups with benzoyl groups followed by deprotecting the 2', 3', and 5' positions of the ribofuranose ring; and (iv) protecting hydroxyl groups at 3' and 5' positions of the ribofuranose ring, removing a hydroxyl group at 2' position of the ribofuranose ring, and then deprotecting 3' and 5' positions of the ribofuranose ring.

* * * * *

UNITED STATES PATENT AND TRADEMARK OFFICE
CERTIFICATE OF CORRECTION

PATENT NO. : 6,350,863 B1
DATED : February 26, 2002
INVENTOR(S) : Mitsuhiko Shionoya et al.

It is certified that error appears in the above-identified patent and that said Letters Patent is hereby corrected as shown below:

Title page,
Item [56], OTHER PUBLICATIONS, "furanosl" should read -- furanosyl --.

Column 1,
Line 10, "No .9-248 787," should read -- No. 9-248787, --.

Column 2,
Line 39, "oligonucleotide" should read -- oligonucleotides --.

Column 3,
Line 36, "o-benzyl" should read -- O-benzyl --.

Column 4,
Line 33, "o-benzyl" should read -- O-benzyl --.

Column 5,
Line 9, "oligonucleotide" should read -- oligonucleotides --.

Column 7,
Line 39, "2,3,5-tri-o-benzyl" should read -- 2,3,5-tri-O-benzyl --.

Column 9,
Line 18, "an" should read -- a --;
Line 48, "OD)" should read -- OD) ¶ --; and
Line 54, "OD)" should read -- OD) ¶ --.

Column 10,
Line 29, "$^{13}$c $^{31}$p $^{195}$Pt)," should read -- $^{13}$C, $^{31}$P, $^{195}$Pt), --; and
Line 37, "a" should read -- an --.

Column 11,
Line 4, "less" should read -- fewer --;
Lines 17-28,

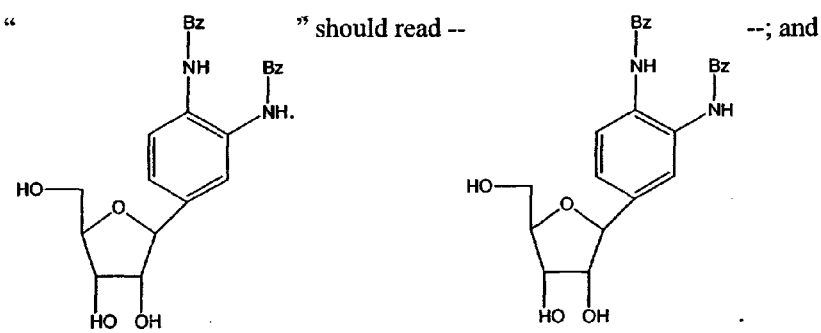

UNITED STATES PATENT AND TRADEMARK OFFICE
CERTIFICATE OF CORRECTION

PATENT NO.    : 6,350,863 B1
DATED         : February 26, 2002
INVENTOR(S)   : Mitsuhiko Shionoya et al.

It is certified that error appears in the above-identified patent and that said Letters Patent is hereby corrected as shown below:

Column 11 cont'd,
Line 31, "formula (11)" should read -- formula (11): --.
Lines 34-45,

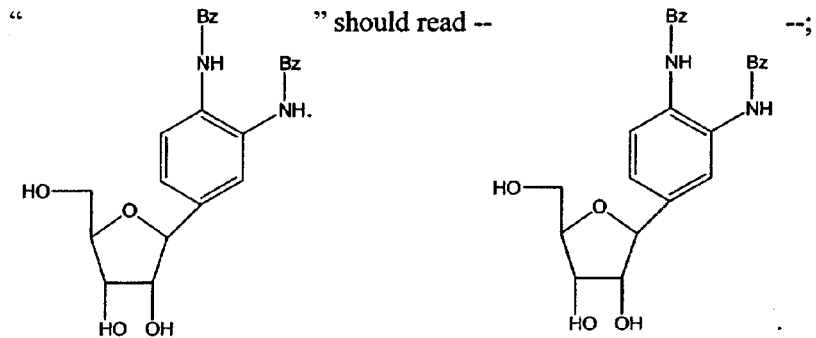

Line 29, "formula (12)" should read -- formula (12): --; and
Line 47, "(i) obtaining" should read -- comprising the steps of: ¶
                                                    (i) obtaining --.

Signed and Sealed this

Seventeenth Day of December, 2002

JAMES E. ROGAN
*Director of the United States Patent and Trademark Office*